United States Patent [19]

Schumaker

[11] Patent Number: 5,237,067

[45] Date of Patent: Aug. 17, 1993

[54] OPTOELECTRONIC TAUTOMERIC COMPOSITIONS

[76] Inventor: Robert R. Schumaker, #66 Cincunvalcion, Poniente, #12 Cuidad Granja, Guadalajara, Mexico

[21] Appl. No.: 830,833

[22] Filed: Feb. 4, 1992

[51] Int. Cl.$^5$ ............... C07D 211/70; C07D 207/20; C07D 409/14; C07D 421/14

[52] U.S. Cl. .................... 546/187; 548/523; 549/19; 549/36

[58] Field of Search ........... 546/187; 548/523; 549/19, 36

[56] References Cited

U.S. PATENT DOCUMENTS 3,410,842 11/1968 Allais et al. ............. 548/523 X
4,755,323 7/1988 Eidenschink et al. ........ 546/187 X

FOREIGN PATENT DOCUMENTS 0611336 12/1960 Canada ................. 548/523
3408327 9/1985 Fed. Rep. of Germany ...... 546/187
47-26787 7/1972 Japan ................... 546/187
0432145 7/1975 U.S.S.R. ................. 546/187

Primary Examiner—Marianne M. Cintins
Assistant Examiner—Michael B. Hydorn

[57] ABSTRACT

This application is directed to optoelectronic materials which are bistable organic tautomeric compositions of dithio or diseleno carbamate esters of cyclic 1,3-dithia or -diselena-2-iminium salts. Specifically, it is concerned with compounds having the formula:

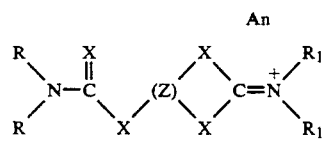

Wherein X is S or Se; wherein R or $R_1$ are alkyl, or alkyl that together form a ring of carbon atoms; wherein An is the anion of a strong acid. These molecules are in themselves molecular-sized optoelectric switching devices.

5 Claims, No Drawings

OPTOELECTRONIC TAUTOMERIC COMPOSITIONS

BACKGROUND OF THE INVENTION

1. Field of the Invention

This invention relates to a class of novel valence tautomeric compounds which are, in themselves, optoelectronic switching devices. More specifically, these intramolecular devices are dichalcogenide carbamate esters of dichalcogenide onium salts, compounds that are capable of undergoing valence tautomerism between degenerate cationic tautomeric forms which are optically active and enantiomeric to each other. This invention provides a class of optoelectronic compositions which can be resolved and arranged as a type of molecular switching device useful in molecular electronics.

2. Related Art

Certain 4-(N,N-dialkyldithiocarbamato)-2-alkyliminio-1,3-dithietanes have been found to exhibit valence tautomerism via a ring-opening/ring-closing reaction [R. R. Schumaker et al., *J. Chem. Soc., Chem. Commun*, 1991, 719], as shown in the following mechanism (scheme 1).

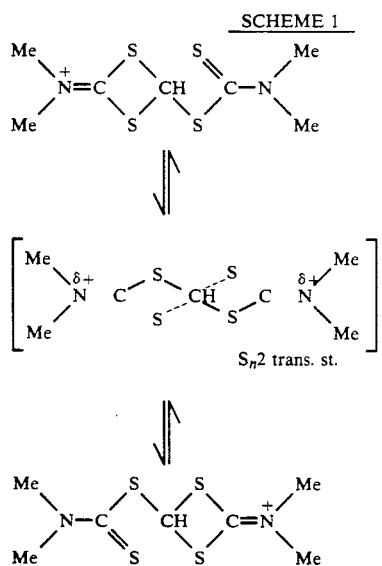

The "$^1$H" NMR spectra of the above compound in solution provided evidence for the degenerate rearrangement between the two equivalent tautomers.

This type of intramolecular conversion would be possible between optically active tautomeric forms of molecules structurally similar to those valence tautomeric compounds described above. Such molecules, if optically resolved and assembled can be made to function as an optoelectric switching device.

SUMMARY OF THE DISCLOSURE

This invention provides molecular-sized optoelectric devices which are a class of novel cationic valence tautomeric compounds of the formula:

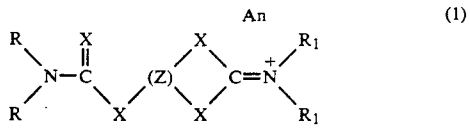

wherein An is the anion of a strong acid; wherein X is sulfur or selenium; wherein the R and $R_1$ groups are alkyl or cycloalkyl and may be variously substituted; and the Z element is a chiral ring-completing group of atoms which change chirality on tautomerization.

The inventive switch mechanism of this intramolecular device is the ring-opening, ring-closing tautomerism between 1,3-dichalcogenide-2-iminium cations and dichalcogenide carbamoyl esters that reverses two molecular properties; the molecular electric dipole moment and the molecular optical activity.

Prototype molecular devices have been prepared, each of the inventive structure and each capable of undergoing, at various rates, optoelectronic switching between enantiomeric ions. These molecules illustrate variations in size and composition of the Z, R, and An constituents useful for aligning and tuning the molecular devices.

The possible structures for the Z portion of the device is governed by the requirement of enantiotropic tautomerism—or —'psuedoenantiotropic' tautomerism when $R \neq R^1$ of formula (1).

DETAILED DESCRIPTION OF THE INVENTION

Generally, in the above formula (1) X is preferably sulfur and An is preferably selected from the group consisting of hexafluorophosphate, tetraphenylborate, bromide or chloride.

A first preferred group of compounds of this invention consists of the compounds of the formula (1), wherein Z is —CH—CH$_2$—; and the R groups together with the nitrogen form pyrrolidinyl or piperidinyl groups.

Preferred individual compounds of the formula (1) are:

4-(pyrrolidinyldithiocarbamato)-2-pyrrolidinium-1,3-dithialane hexafluorophosphate;

4-(N,N-dimethyldithiocarbamato)-2-dimethyliminium-1,3-dithialane hexafluorophosphate;

4-(piperidinyldiselenocarbamato)-2-piperidinium-1,3-diselenalane tetraphenylborate; and, 4-(N,N-dimethyldithiocarbamato)-2-dimethyliminium-1,3,5-trithiane hexafluorophosphate.

The overall synthetic procedure for the preparation of compounds of this invention is illustrated (Scheme 2, next page) by way of a synthetic sequence leading to a preferred compound of formula (VII) wherein Z is —CH—CH$_2$—.

In Scheme 2, R may be alkyl or cycloalkyl; X may be S or Se; M represents alkali metal or dialkyl ammonium (e.g., dimethylammonium, piperidinium or pyrrolidinium).

4-(pyrrolidinyldithiocarbamato)-2-pyrrolidinium-1,3-dithialene hexafluorophosphate;

4-(N,N-dimethyldithiocarbamato)-2-dimethyliminium-1,3-dithiolane hexafluorophosphate;

4-(piperidinyldiselenocarbamato)-2-piperidinium-1,3-diselenalane tetraphenylborate; and 4-(N,N-dimethyldithiocarbamato)-2-dimethyliminium-1,3,5-trithiane hexafluorophosphate.

The overall synthetic procedure for the preparation of compounds of this invention is illustrated (scheme 2) below by way of a synthetic sequence leading to a preferred compound of formula (VII) wherein Z is —CH—CH$_2$—.

SCHEME 2

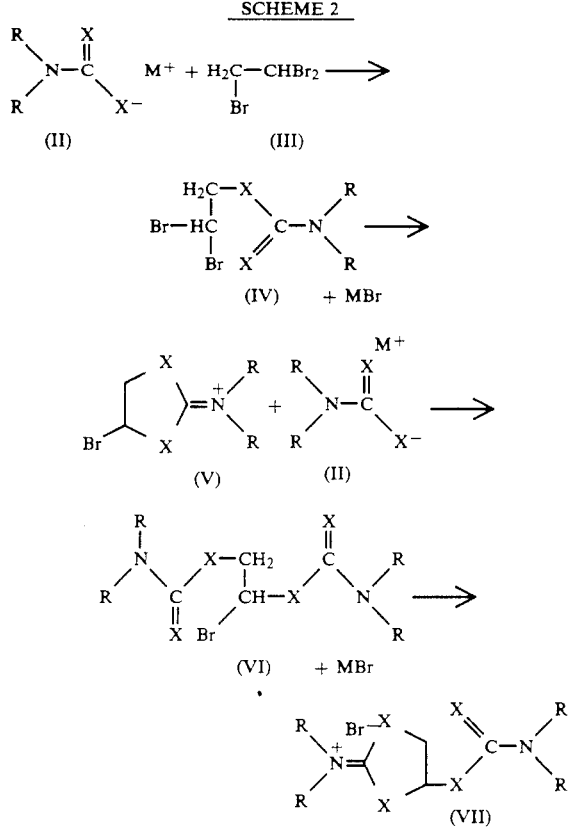

In Scheme 2, R may be alkyl or cycloalkyl; X may be S or Se;

In the first step of the above reaction sequence, one molar equivalent of compound (II) is condensed with 1,1,2-tribromoethane (III) to provide a transient halogenated intermediate (IV). A second molar equivalent of compound (II) is condensed with the intermediate (IV) to produce a second transient halogenated intermediate (VI), which undergoes cyclization to afford a compound of formula (VII). While these steps may not require a solvent, a reaction-inert solvent can be employed without adversely affecting the condensation. Typically, reaction is exothermic and complete within one to two hours.

In practice, the compounds (II) and (III) are combined and heated initially to about 60° C. The ensuing exothermic reaction is controlled at around 100° C., and further heating provides the compound (VII) directly.

The compound of the formula (VII) wherein An is bromo can be converted to other acid anion salts of the formula (VII). For example, the acid HAn or its equivalent anion An- is added to an aqueous solution containing an equivalent amount of the compound (VII) wherein An is bromo. The final salts (VII) wherein An is replaced by other anions may be obtained by precipitation or by evaporation of the solvent. Purification can be carried by recrystallization. Preferably, An represents PF$^-_6$ Ph$_4$B$^-$, Br$^-$, or Cl$^-$.

Starting reagents (II) and (III) for the compounds (VII) of the present invention are either commercially available or can readily be prepared by the herein described procedures, their modification or procedures known to those skilled in the art.

The compounds (I) of the present invention are asymmetric and therefore capable of existing in two optically active enantiomeric forms. The racemic forms of the compounds (I) are generally capable of resolution into the optically active forms by the classic method of forming diastereomeric salts with chiral acids, now separable by fractional crystallization or by column chromatography using optically active stationary phases. For example, resolution of iminium salts formed from chiral acids as described in W.R. Adams, J. Am. Chem. Soc., 1965, 88, 102, may be employed. Most conveniently, the resolution of the present compounds (I) can be accomplished by ion exchange of the racemic mixtures thereof with optically active anions to form diastereomeric pairs of salts. In practice, the perchlorate salts of the racemic mixtures are exchanged with potassium d-camphor-10-sulfonate from absolute methanol solutions. Recrystallization from acetone-hexane of the residual mixtures provides the pure diastereomeric salts. An unwanted diastereoisomer can be racemized and recycled. The d-camphor-10-sulfonate anions can subsequently be exchanged by treatment with sodium tetraphenylborate in methanol to precipitate the enantiomeric tautomeric forms as tetraphenylborate anion salts. The present invention encompasses the racemic modifications of the compounds of the formula (I), the diastereomeric mixtures, the pure enantiomers and diastereomers thereof.

The individual molecules of the formula (I) wherein X is sulfur or selenium contain optically active dichalcogenide iminium ring systems and dichalocogenide carbamate substituents which are capable of undergoing a ring-opening, ring-closing valence tautomerism between stereoisomeric forms ("stereotropic tautomerism"). When the tautomeric forms are enantiomeric to each other, the tautomerism is termed as "enantiotropic tautomerism."

Such enantiomeric tautomerism is illustrated below in the case of a preferred compound (VIII) (scheme 3).

SCHEME 3

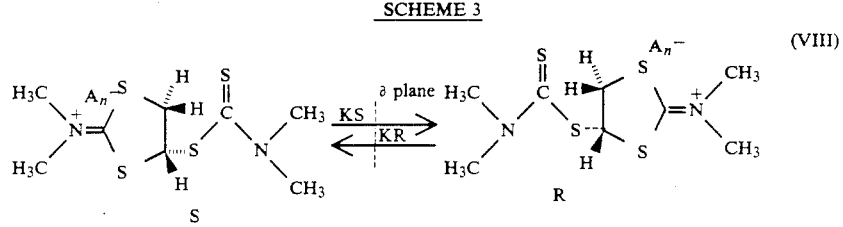

The energy profile for the tautomerism between the enantiomeric cations is that of a symmetrical double-welled potential energy curve. The shape of this curve is determined by an energy barrier, Ei, that separates the tautomeric forms. In the absence of distorting energy fields, the rate constants "$K_R$" and "$K_S$" for interconversion between the enantiomeric forms are equal and expected to have Arrhenius temperature dependence, $k = k_{-1} = A\exp(-Ei/RT)$, where Ei is the energy barrier of interconversion, T is the temperature, R is the universal gas constant and A is a frequency factor. The height or magnitude of the energy barrier (Ei) is dependent on the particular ring system undergoing tautomerism and as such is a function of such factors as ring size, substituents and heteroatom incorporation.

In the presence of asymmetrical energy fields as produced by electric, magnetic or non-symmetrical environments, a distortion of the energy profile diagram occurs. This distortion produces an energy preference for one molecular form over the other molecular form or, in other words, an inequality between the interconversion rate constants "$K_R$" and "$K_S$".

Thermal equilibration of the two forms commutes the molecular switching device in favor of the optical tautomer of lower energy. The state of the device is determined by measuring the circular birefringence or dichroism of an imposed laser beam. The utility of optically active compounds of the formula (1) is apparent to one skilled in the art in molecular electronics as optoelectric switching devices.

1. Molecular Optoelectric Switching Device

The controlled tautomerism induced by site selective irradiation of an array of optically active molecules of this invention and the detection of specific optical states by their rotatory effect on polarized light constitutes a molecular-optical data storage device. The functioning of the molecular device involves the following protocol.

(a) Resolution of a racemic mixture of the present compounds into optically active forms.
(b) Orientations and fixation of one optical form. This step is used to align and maintain both the molecular dipole moment and optical axis of one enantiomeric form with respect to an external reference system. It may be accomplished by a variety of techniques in various media, including LB films, self-assembled covalent attachment and poled polymers, which are well known to one skilled in the art (T. J. Marks et al., J. Am. Chem. Soc., 1990, 112, 7389).
(c) Incorporation of a system for the distorting of molecular energy profiles of oriented molecules. The distortion of potential energy profiles by the imposition of electrical magnetic or electro-magnetic force fields can be accomplished by known methods (A. Aviran and P. E. Seiden, U.S. Pat. No. 3,833,894 (1974).
(d) Reversal of the optical activity and molecular dipole by inducing tautomerism of the molecules by laser irradiation. Equilibration between the energetically distorted forms of the molecules can be realized by illumination at frequencies determined to stimulate vibrationally or thermally active modes.
(e) Incorporation of a system for determination of the optical activity of the tautomers. The reflection or transmission of polarized light of lasers from the molecules will be analyzed by a system of polarizers and photocells to measure the sign and degree of rotatory effects for the determination of tautomeric states of the molecules (see, I. J. Lalov, et al., J. Chem. Phys., 1986, 85, 5505). For enhanced detection advantage can be taken of the circular dichroism (Cotton effect) observed with chromophores associated with optical centers.

In the functioning of the present molecules as optoelectric devices, the controlled intraconversion of the oriented and fixed tautomers (steps (a) and (b)) by the imposition of a potential energy distortion (step (c)) combined with laser stimulation (step (d)) constitutes a a switching device that is detected by the sign of the rotatory effect of the respective tautomers on the plane of polarized light (step (e)). In practice, a substrate such as a polymer film is prepared according to step (a) by fixing molecules of this invention thereon. The substrate is then incorporated as the above-described device.

EXAMPLE 1

General Identification Of Optically Active Molecular Devices

All optically active molecular device examples conform to the general structure provided and can be further identified by their capacity to undergo a ring-opening, ring-closing tautomerism between stereoisomeric forms. Individual molecular structure was identified by one or more methods including x-ray analysis, chemical analysis, proton nuclear magnetic resonance and infrared spectra. The molecules exhibit characteristic proton magnetic resonances for both the iminium and the carbamate substituents between 3.0 and 4.0 ppm. These substituents also have characteristic infrared absorptions for the carbamate group at ca 1500 cm$^{-1}$ and the iminium group between 1500–1700 cm$^{-1}$. Characteristic ultraviolet absorptions for the dithiocarbamate substituent $V_{max}$(EtOH) of approximately 255 and 278 nm were observed.

EXAMPLE 2

R, S-4-(pyrrolidinyldithiocarbamato)-2-pyrrolidinium-1,3-dithialane hexafluorophosphate.

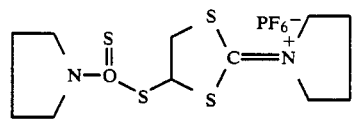

To 25 ml of 1,1,2-tribromoethane was added 13.0 g of pyrrolididinecarbodithioic acid pyrrolidinium salt and the mixture heated with stirring to 60° where an exothermic reaction was observed. The exotherm was controlled below 100° by application of a water bath. The solution was then heated to 115° and the temperature maintained for 15 minutes. Addition of the cooled solution to ether (1 liter) precipitated the crude bromide salt as a dark oil which slowly crystallized. The ether was decanted and the product washed with additional ether and extracted into water (1 liter). Addition of an aqueous solution of hexafluorophosphate (5.50 g) provided 7.75 gr (83.5% based on 3:1 stoichiometry) of the title compound as a white powder. Crystallization from acetone-hexane provided an analytical sample as colorless needles, m.p. 197°–198° C.

Anal. Calcd. for $C_{12}H_{19}N_2S_4PF_6$: C, 31.03; H, 4.07; N, 6.03; S, 27.59. Found: C, 31.14; H, 4.12; N, 5.98; S, 27.48.

$^1$H-nmr (ppm, $d_6$-acetone): 6.35 dd (1, $C_4H$, J=1.9, 5.3 Cps), 4.53 dd (1, $C_5H$, J=5.5, 13.3 cps), 4.31 dd (1, $C_5H$, J=2.0, 13.3 cps), 3.5-4.0 (m, 8, -pyrrolidinyl), 1.9-2.2 (m, 8, -pyrrolidinyl).

IR (KBr): 1480 (s, iminium), 1444 (s, carbamate), 835 cm$^{-1}$ (s, $PF_6^-$).

EXAMPLE 3

R, S-4-(N,N-dimethyldithiocarbamato)-2-dimethyliminium-1,3-dithialane hexafluorophosphate.

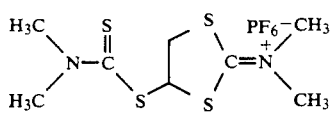

Reaction of N,N-dimethyldithiocarbodithioic acid sodium salt dihydrate (5 g) with 1,1,2-tribromoethane (20 ml) as described in Example 2, provided 2.2 g of the title compounds as white microcrystals, m.p. 200°-204° C.

$^1$H-nmr (ppm, $d_6$-acetone): 6.35 (dd, 1, $C_4$), 4.65 (dd, 1, $C_5$), 4.35 (dd, 1, $C_5$), 3.72 (s, 3, iminium methyl), 3.68 (s, 3, iminium methyl), 3.52 (s, 3 carbamate methyl), 3.40 (s, 3, carbamate methyl).

IR (KBr): 1487 (s, iminium), 1383 (carbamate), 834 cm$^{-1}$ (s, $PF_6^-$).

The corresponding tetraphenyl borate salt was obtained as colorless needles, m.p. 202° C. (decomposition).

EXAMPLE 4

R, S-4-(piperidinydiselenylcarbamato)-2-piperidinium-1,3-diselenalane tetraphenylborate.

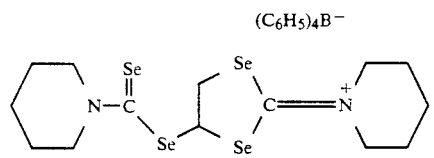

Reaction of piperidinecarbodiselenoic acid piperidinium salt (3.60 g) with 1,1,2-tribromoethane (5 ml) as described above in Example 2, provided 1.50 g of the title compound as a white powder, m.p. 128°-130° C.

$^1$H-nmr (ppm, $D_3$-acetonitrile) 6.4 (m, 1, $CH_4$), 4.3 (m, 2, $CH_2$)m 3.4-3.9 (m, 8, alpha-piperidinyl), 1.70 (m, 12, beta-piperidinyl).

EXAMPLE 5

R,S-4-(N,N-dimethyldithiocarbamato)-2-dimethyliminium-1,3,5-trithiane hexafluorophosphate.

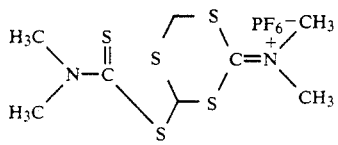

Reaction of N,N-dimethyldithiocarbodithioic acid sodium salt (5 g) with 1,1,3-trichloro-2-thiopropane (12 ml) as described above in Example 2, provided 1.0 g of the title compound, m.p. 178°-179° C.

IR (KBr): 1574 (s, iminium), 1398 (s, carbamate), 830 cm$^{-1}$ (s, $PF_6^-$).

The invention now being fully described, it will be apparent to one of ordinary skill in the art that many changes and modifications can be made without departing from the spirit or scope of the invention.

I claim:

1. Valence tautomeric compounds which are dialkyldithiocarbamato or dialkyldiselenocarbamato esters of 1,3-dithia or 1,3-diselenacyclo-2-dialkyliminium salts having the formula:

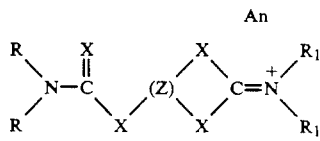

wherein X is S or Se; wherein the R are lower alkyl or taken together with the N form a piperidine or pyrrolidine ring; wherein Z is a —CH$_2$—CH— carbon bridge or a —CH$_2$—S—CH— bridge; and An is the anion of a strong acid.

2. R, S,-4-(pyrrolidinyldithiocarbamato)-2-pyrrolidinium-1,3-dithialane salts of strong acids having the formula:

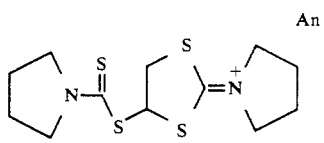

wherein An is the anion of a strong acid.

3. R, S-4(N,N-dimethyldithiocarbamato)-2-dimethyliminium-1,3-dithialane salts of strong acids having the formula:

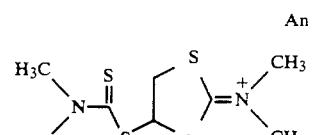

wherein An is the anion of a strong acid.

4. R,S-4-(piperidinyldiselenocarbamato)-2-piperidinium-1,3-diselenalane salts of strong acids having the formula:

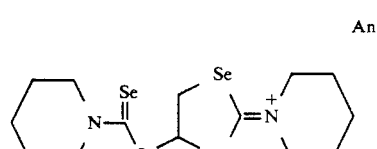

wherein An is the anion of a strong acid.

5. R,S-4-(N,N-dimethyldithiocarbamato)-2-dimethyliminium-1,3,5-trithiane salts of strong acids having the formula:

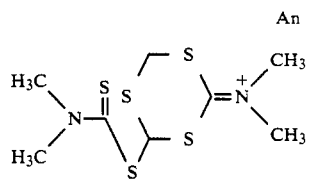
wherein An is the anion of a strong acid.
* * * * *